United States Patent [19]

Kranz et al.

[11] Patent Number: 4,530,715
[45] Date of Patent: Jul. 23, 1985

[54] CYCLOALKYL (α-TRIAZOLYL-β-HYDROXY)-KETONES AS FUNGICIDES AND PLANT GROWTH REGULATORS

[75] Inventors: Eckart Kranz, Wuppertal; Karl H. Büchel, Burscheid; Udo Kraatz, Leverkusen; Erik Regel, Wuppertal; Wilhelm Brandes, Leichlingen; Paul-Ernst Frohberger, Leverkusen; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 438,448

[22] Filed: Nov. 2, 1982

[30] Foreign Application Priority Data

Nov. 19, 1981 [DE] Fed. Rep. of Germany ....... 3145846

[51] Int. Cl.³ .................. A01N 43/64; A01N 55/02; C07D 249/08; C07F 3/00
[52] U.S. Cl. .......................... 71/76; 71/92; 548/262
[58] Field of Search ............... 548/262, 101; 424/245, 424/269; 71/76, 92

[56] References Cited

U.S. PATENT DOCUMENTS 4,217,129  8/1980  Shephard et al. .................. 548/262
4,291,047  9/1981  Kranz et al. ....................... 548/262

FOREIGN PATENT DOCUMENTS 0007505  2/1980  Fed. Rep. of Germany ...... 548/262
3002430  7/1981  Fed. Rep. of Germany ...... 424/269

Primary Examiner—Alton D. Rollins
Attorney, Agent, or Firm—Sprung Horn Kramer & Woods

[57] ABSTRACT

Cycloalkyl (α-triazolyl-β-hydroxy)-ketones of the general formula

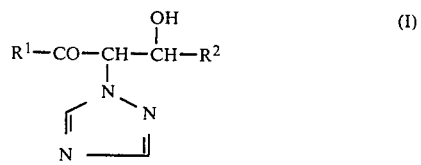

in which $R^1$ represents an optionally substituted cycloalkyl group, and $R^2$ represents a halogenoalkyl, halogenoalkenyl or alkoxycarbonyl group, and their physiologically acceptable acid addition salts and metal salt complexes are new, are prepared as described and find use as fungicides and plant growth regulators.

12 Claims, No Drawings

CYCLOALKYL (α-TRIAZOLYL-β-HYDROXY)-KETONES AS FUNGICIDES AND PLANT GROWTH REGULATORS

The present invention relates to certain new cycloalkyl(α-triazolyl-β-hydroxy)-ketones, to a process for their production, and to their use as fungicides and plant growth regulators.

It has already been disclosed that certain alkyl or phenyl(α-triazolyl-β-hydroxy)-ketones possess a good fungicidal activity (see U.S. Pat. No. 4,291,047.) Thus, for example, 1,1,1-trichloro-2-hydroxy-3-(1,2,4-triazol-1-yl)-4-(4-chlorophenyl)-butan-4-one, 2-chloro-3-hydroxy-2,7,7-trimethyl-4-(1,2,4-triazol-1-yl)-heptan-5-one and 1,1,1-trichloro-2-hydroxy-5,5-dimethyl-3-(1,2,4-triazol-1-yl)-hexan-4-one can be used for combating fungi. However, the action of these compounds is not always completely satisfactory, in particular when low amounts and concentrations are used.

The present invention now provides, as new compounds, the cycloalkyl(α-triazolyl-β-hydroxy)-ketones of the general formula

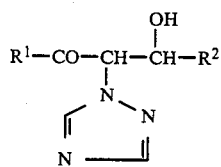

in which $R^1$ represents an optionally substituted cycloalkyl group, and $R^2$ represents a halogenoalkyl, halogenoalkenyl or alkoxycarbonyl group, and the physiologically acceptable acid addition salts and metal salt complexes thereof.

The compounds according to the invention, of the formula (I), possess two asymmetric carbon atoms; they can therefore be present in the erythro as well as in the threo form. They are obtained in general as diastereomer mixtures of varying composition. In all cases, they are predominantly present as racemates.

According to the present invention there is further provided a process for the production of a compound of the present invention characterized in that an α-triazolyl-ketone of the general formula

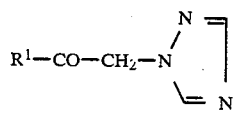

in which $R^1$ has the meaning given above, is reacted with an aldehyde of the general formula

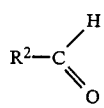

or a hydrate or semi-acetal thereof, in which $R^2$ has the meaning given above, in the presence of a diluent and in the presence of a catalyst, and, if desired, the product is then converted into an addition product thereof with an acid or a metal salt.

Finally, it has been found that the new cycloalkyl(α-triazolyl-β-hydroxy)-ketones of the formula (I), and their acid addition salts and metal salt complexes, possess powerful fungicidal and plant growth regulating properties.

Surprisingly, the substances according to the invention exhibit a better fungicidal activity than the compounds 1,1,1-trichloro-2-hydroxy-3-(1,2,4-triazol-1-yl)-4-(4-chlorophenyl)-butan-4-one, 2-chloro-3-hydroxy-2,7,7-trimethyl-4-(1,2,4-triazol-1-yl)-heptan-5-one and 1,1,1-trichloro-2-hydroxy-5,5-dimethyl-3-(1,2,4-triazol-1-yl)-hexan-4-one, which are known from the prior art and which are constitutionally similar substances having a similar action. In addition, the substances according to the invention unexpectedly are also distinguished by very good plant growth regulating properties.

Preferred cycloalkyl(α-triazolyl-β-hydroxy)-ketones according to the present invention are those, in which $R^1$ represents a cycloalkyl group which has 3 to 8 carbon atoms and which is optionally substituted by alkyl having 1 to 6 carbon atoms, and $R^2$ represents a straight-chain or branched halogenoalkyl group having 1 to 4 carbon atoms and 1 to 5 identical or different halogen atoms (such as, especially, fluorine, chlorine or bromine), a straight-chain or branched halogenoalkenyl group having 2 to 4 carbon atoms and 1 to 5 identical or different halogen atoms (such as, especially, fluorine, chlorine or bromine) or an alkoxycarbonyl group having 1 to 4 carbon atoms in the alkoxy part.

Particularly preferred compounds of the present invention are those, in which $R^1$ represents a cyclopentyl, cyclohexyl or cyclopropyl group which is optionally substituted by methyl, ethyl or propyl, and $R^2$ represents a trichloromethyl, dichlorofluoromethyl, trifluoromethyl, dichloromethyl, chloromethyl, 1,1,2-trichloroethyl, 1,1-dichloroethyl, 1,1-dibromoethyl, 1,1-dichloropropyl, 1,1-dichlorobutyl, 1,1,2-trichloropropyl, 2-chloro-prop-2-yl, 1,2,2-trichlorovinyl, 2,2-dichlorovinyl, 1,1-dichloro-2-methylpropyl, methoxycarbonyl or ethoxycarbonyl group.

In addition to the compounds given in the preparative examples, the following compounds of the general formula (I) may be mentioned individually:

TABLE 1

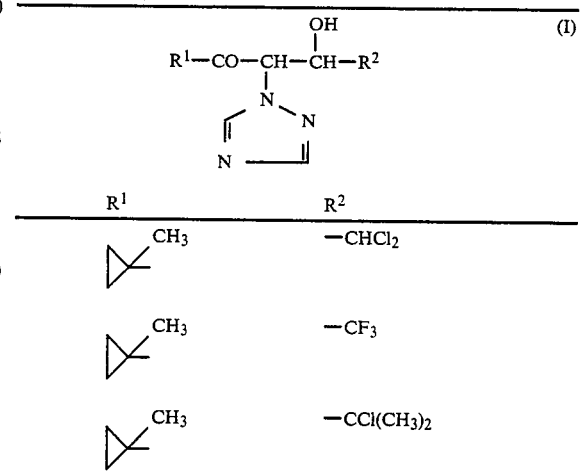

TABLE 1-continued $$R^1-CO-\overset{\underset{|}{N\diagup\!\!\!\!\diagdown\!\!N}}{\underset{N\!\!-\!\!\!\|}{CH}}-\overset{OH}{\underset{|}{CH}}-R^2 \quad (I)$$

| R¹ | R² |
|---|---|
| cyclopropyl-CH₃ | —CH=CCl₂ |
| cyclopropyl-CH₃ | —COOCH₃ |
| cyclopropyl-CH₃ | —COOC₂H₅ |
| cyclopropyl-CH₃ | —CCl₂CH(CH₃)₂ |
| cyclopropyl-C₂H₅ | —CCl₃ |
| cyclopropyl-C₂H₅ | —CCl₂CH₂Cl |
| cyclopropyl-C₂H₅ | —CCl₂CH₃ |
| cyclopropyl-C₂H₅ | —CCl₂CHClCH₃ |
| cyclopropyl-C₂H₅ | —CHCl₂ |
| cyclopropyl-C₂H₅ | —CCl₂CH(CH₃)₂ |
| cyclohexyl-H | —CCl₃ |
| cyclohexyl-H | —CHCl₂ |
| cyclohexyl-H | —CCl₂CH₃ |
| cyclohexyl-H | —CCl₂CH₂Cl |
| cyclohexyl-H | —CCl₂CHClCH₃ |
| cyclohexyl-H | —CCl₂CH(CH₃)₂ |

The preferred and particularly preferred compounds according to the invention, of course, include addition products of acids with cycloalkyl(α-triazolyl-β-hydroxy)-ketones of the formula (I) in which the radicals $R^1$ and $R^2$ have the meanings which have already been respectively mentioned.

The acids with which addition products may be formed include, as preferences, hydrohalic acids (such as hydrobromic acid and, especially, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and naphthalene-1,5-disulphonic acid).

The preferred and particularly preferred compounds according to the invention, of course, also include addition products of salts of metals of main groups II to IV and of sub-groups I and II and IV to VIII and those cycloalkyl(α-triazolyl-β-hydroxy)-ketones of the formula (I) in which $R^1$ and $R^2$ have the meanings which have already been respectively mentioned.

In this context, salts of copper, zinc, manganese, magnesium, tin, iron and nickel are particularly preferred. Suitable anions of these salts are anions which are derived from those acids which lead to physiologically acceptable addition products. In this connection, particularly preferred acids of this type are the hydrogen halides (such as hydrochloric acid and hydrobromic acid) and also phosphoric acid, nitric acid and sulphuric acid.

If, for example, 1-methyl-1-(1,2,4-triazol-1-yl)-acetyl)-cyclopropane and chloral are used as starting materials, the course of the reaction in the process according to the invention can be represented by the following equation:

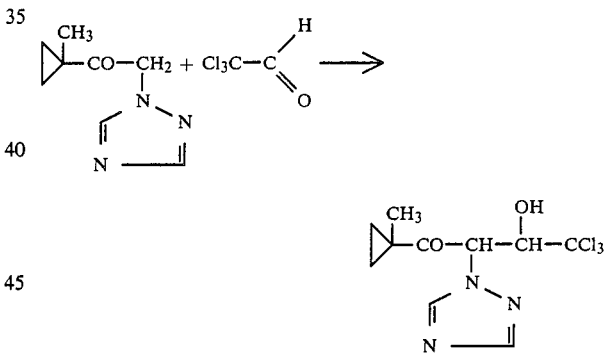

Preferred α-triazolyl-ketones of formula (II) to be used as starting materials for the process according to the invention are those in which $R^1$ has those meanings which have already been mentioned for this substituent in connection with the description of the preferred and particularly preferred compounds according to the present invention.

Some of the α-triazolyl-ketones of the formula (II) are known (see U.S. patent application Ser. No. 291,700, filed Aug. 10, 1981 and DE-OS (German Published Specification) No. 3,010,560).

The following general formula:

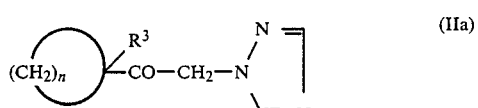

in which:

$R^3$ represents an alkyl group, especially an alkyl group having 1 to 6 carbon atoms, and n is an integer from 3 to 7, gives a definition of the hitherto unknown α-triazolyl-ketones.

The hitherto unknown α-triazolyl-ketones of the formula (IIa), which form the subject of a separate patent application can be prepared by a process in which halogen compounds of the formula

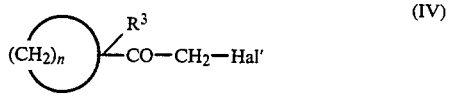

in which $R^3$ and n have the meanings given above, and

Hal' represents a chlorine or bromine atom, is reacted with 1,2,4-triazole of the formula

in the presence of an inert organic solvent and in the presence of an acid-binding agent.

The halogen compounds of the formula (IV) which are required as starting materials in the above reaction for the preparation of the α-triazolyl-ketones of the formula (IIa) were hitherto unknown. However, they can be prepared in a simple manner according to processes which are known in principle.

Thus, the halogen compounds of the formula (IV) are obtained, for example, by adding chlorine or bromine to ketones of the general formula

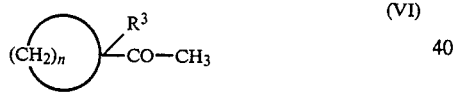

in which $R^3$ and n have the meanings given above, in the presence of an inert organic solvent at room temperature; or by reacting these ketones, for example, with customary chlorinating agents (such as sulphuryl chloride) at 20° to 60° C.

The ketones of the formula (VI) are obtained by reacting nitriles of the general formula

in which $R^3$ and n have the meanings given above, in the customary manner with an organometallic compound (such as, especially, methyl magnesium bromide) in the presence of a diluent (such as anhydrous ether), at a temperature between 0° and 80° C.

The nitriles of the formula (VII) are known (see Journal of Organometallic Chemistry 57, C 33–35 1 (1973)), and they can be obtained by the process given in this publication.

Any of the inert organic solvents are suitable diluents in the preparation of the α-triazolyl-ketones of the formula (IIa) by the above process. Preferred solvents are nitriles (such as acetonitrile), ketones (such as acetone and methyl n-butyl ketone), alcohols (such as ethanol, propanol and n-butanol) aromatic hydrocarbons (such as toluene) and polar solvents (such as dimethylformamide and dimethylsulphoxide).

Any of the inorganic and organic bases which are customarily used for reactions of this type can be employed as acid-binding agents in the preparation, described above, of the α-triazolyl-ketones of the formula (IIa). Alkali metal carbonates (such as sodium carbonate and potassium carbonate or sodium bicarbonate) and also lower tertiary alkylamines, aralkylamines, aromatic amines or cycloalkylamines (such as triethylamine, dimethylbenzylamine, pyridine, 1,5-diaza-bicyclo[4.3.0]non-5-ene (DBN) and 1,8-diaza-bicyclo[5.4.0]undec-7-ene (DBU)), may preferably be used. However, it is also possible to employ an appropriate excess of 1,2,4-triazole.

In the above process for the preparation of the α-triazolyl-ketones of the formula (IIa), the temperatures can be varied within a relatively wide range. In general, the reaction is carried out at a temperature between 20° C. and 120° C., preferably between 40° and 90° C.

In carrying out the above process for the preparation of the α-triazolyl-ketones of the formula (IIa), 1 mol, or even an excess, of 1,2,4-triazole of the formula (V) is employed in general per mol of halogen compound of the formula (IV). The working-up is effected according to customary methods.

The remaining compounds of the formula (II) may also be prepared as described for the α-triazolyl-ketones of the formula (IIa).

Preferred aldehydes of formula (III) additionally to be used as starting materials for the reaction according to the invention are those in which $R^2$ has those meanings which have already been mentioned for this substituent in connection with the description of the preferred and particularly preferred compounds according to the invention.

The aldehydes of the formula (III) are generally known compounds of organic chemistry.

Preferred diluents for the reaction according to the invention are inert organic solvents. These include, as particular preferences, alcohols (such as methanol and ethanol) and mixtures thereof with water, ethers (such as tetrahydrofuran and dioxane), nitriles (such as acetonitrile and propionitrile), halogenated aliphatic and aromatic hydrocarbons (such as methylene chloride, carbon tetrachloride, chloroform, chlorobenzene and dichlorobenzene), an glacial acetic acid.

The reaction according to the invention is carried out in the presence of a catalyst. Any of the customarily usable acidic and, in particular, basic catalysts can be employed. These include, as preferences, Lewis acids (such as iron(III)chloride, iron(III)bromide, boron trifluoride, boron trichloride, tin tetrachloride or titanium tetrachloride), alkali metal hydroxides and alkaline earth metal hydroxides (such as potassium hydroxide, sodium hydroxide, calcium hydroxide or barium hydroxide), alkali metal salts (such as potassium carbonate, sodium carbonate, potassium cyanide, secondary sodium phosphate, sodium acetate and sodium sulphite), and alcoholates (such as sodium methylate or potassium methylate).

In carrying out the process according to the invention, the reaction temperatures can be varied within a relatively wide range. In general, the reaction is carried out at a temperature between 0° C. and 100° C., preferably at room temperature or at the boiling point of the particular solvent.

In carrying out the process according to the invention, the reactants of the formulae (II) and (III) are employed in general in equimolar amounts. In addition, a catalytic, or even equimolar, amount of a catalyst is added. It is also possible to employ one of the reactants of the formulae (II) and (III) in an excess. The isolation of the compounds of the formula (I) is effected in the customary manner (see, also, the preparative examples).

The cycloalkyl ($\alpha$-triazolyl-$\beta$-hydroxy)-ketones of the formula (I) which can be prepared by the process according to the invention can be converted into acid addition salts or metal salt complexes.

Those acids which have already been mentioned in connection with the description of the preferred acid addition salts of the compounds of the formula (I) are preferred for the preparation of physiologically tolerated acid addition salts of the substances of the formula (I).

The acid addition salts of the compounds of the formula (I) can be obtained in a simple manner by customary methods of salt formation, for example by dissolving a compound of the formula (I) in a suitable inert solvent and adding the acid, for example hydrochloric acid, and can be isolated in a known manner, for example by filtration, and if appropriate purified by washing with an inert organic solvent.

Those metal salts which have already been mentioned in connection with the description of the preferred metal salt complexes of the compounds of the formula (I) are preferred for the preparation of metal salt complexes of the compounds of the formula (I).

The metal salt complexes of the compounds of the formula (I) can be obtained in a simple manner by customary processes, thus, for example, by dissolving the metal salt in an alcohol, for example in ethanol, and adding the solution to the compound of the formula (I). Metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Dueteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating powder mildew of cucumber (Sphaerotheca fuligina) and powdery mildew of barley (Erysiphe graminis), and for combating Venturia species, such as against the apple scab causative organism (*Venturia inaequalis*), and for combating rice diseases, such as *Pyricularia oryzae*.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at borders, at airports or in fruit orchards. The inhibition of growth of herbaceous and woody plants at borders and in the vicinity of pipelines or overland lines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is a great interest in this action, for example, in the cultivation of tobacco or in the planting of tomatoes.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be reduced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are employed as plant growth regulators, the amounts used can be varied within a relatively wide range. In general, 0.01 to 50 kg, preferably 0.05 to 10 kg, are used per hectare of soil area.

When the substances according to the invention are employed as fungicides, also, the amount used can be varied within a relatively wide range, depending on the type of application. Thus, especially in the treatment of parts of plants, the active concentrations in the use forms are in general between 1 and 0.0001% by weight, preferably between 0.5 and 0.001% by weight. In the treatment of seed, amounts of active compound of 0.001 to 50 g per kg of seed, preferably 0.01 to 10 g, are generally required. For the treatment of soil, active compound concentrations of 0.0001 to 0.1% by weight, preferably 0.0001 to 0.02%, are generally required at the place of action.

The present invention also provides fungicidal or plant growth regulating composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the active compounds according to the invention is illustrated by the following examples.

PREPARATIVE EXAMPLES

EXAMPLE 1

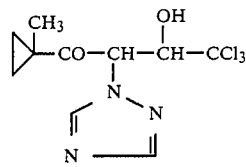

9.2 g (0.0625 mol) of chloral were added dropwise to 8.3 g (0.05 mol) of 1-methyl-1-(1,2,4-triazol-1-yl-acetyl)-cyclopropane, 20 ml of glacial acetic acid and 13.6 g (0.1 mol) of sodium acetate, the internal temperature increasing to approx. 45° C. The reaction mixture was stirred overnight at 80° C. and was thereafter cooled to room temperature and stirred with a mixture of 100 ml of water and 100 ml of ether. The resulting solid was filtered off under suction and recrystallized from methanol. 3.1 g (20% of theory) of 1,1,1-trichloro-2-hydroxy-3-(1,2,4-triazol-1yl)-4-(1-methylcycloprop-1-yl)-butan-4-one of melting point 216° to 218° C. were obtained.

Preparation of the starting material

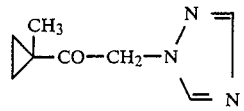

42.5 g (0.24 mol) of 1-bromoacetyl-1-methyl-cyclopropane were added dropwise to a suspension of 27.6 g (0.4 mol) of 1,2,4-triazole and 41.4 g (0.3 mol) of potassium carbonate in 500 ml of acetone at 60° C. After the mixture had been heated for 15 hours at 60° C., the salts were filtered off under suction and the filtrate was evaporated down in vacuo. The residual oil was purified by chromatography (silica gel 60 (Merck)/chloroform).

35.7 g (90% of theory) of 1-methyl-1-(1,2,4-triazol-1-yl-acetyl)-cyclopropane of melting point 58° C. were obtained.

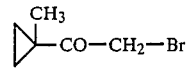

15 ml of bromine, dissolved in 75 ml of chloroform, were added dropwise to a solution of 29.4 g (0.3 mol) of 1-acetyl-1-methylcyclopropane in 150 ml of methyl alcohol at 5° C. The solution was stirred at 10° C. until it was completely decolorized, and was introduced on to ice. The organic phase was washed with water, dried over sodium sulphate, filtered, evaporated down and distilled. 44 g (82.5% of theory) of 1-bromoacetyl-1-methylcyclopropane of boiling point 85° to 90° C./11 mm Hg and of refractive index $n_D^{20} = 1.5002$ were obtained.

EXAMPLE 2

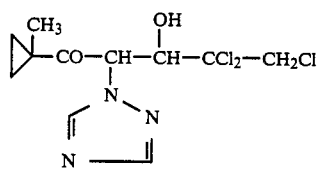

11.3 g of 2,2,3-trichloropropionaldehyde were added dropwise to 9.2 g (0.056 mol) of 1-methyl-1-(1,2,4-triazol-1-yl-acetyl)-cyclopropane in 120 ml of tetrahydrofuran and 13.6 g (0.1 mol) of potassium carbonate, the temperature increasing slightly. The reaction solution was stirred overnight at room temperature and was thereafter introduced into 500 ml of water. The resulting precipitate was filtered off under suction and recrystallized from methanol. 5.5 g (30% of theory) of 1,2,2-trichloro-3-hydroxy-4-(1,2,4-triazol-1-yl)-5-(1-methyl-cycloprop-1-yl)-pentan-5-one of melting point 182° to 186° C. were obtained.

EXAMPLE 3

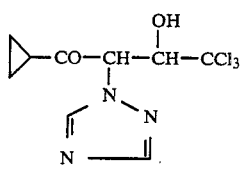

14.8 g (0.1 mol) of chloral were added dropwise to 7.6 g (0.05 mol) of 1,2,4-triazol-1-yl-acetyl-cyclopropane, 7.5 g of glacial acetic acid and 4.1 g (0.05 mol) of sodium acetate, the internal temperature increasing to approx. 42° C. The reaction mixture was stirred for 5 hours at 80° C. and for 12 hours at room temperature, and was then introduced onto water. The resulting precipitate was filtered off under suction and recrystallized from toluene. 8.6 g (57.6% of theory) of 1,1,1-trichloro-2-hydroxy-3-(1,2,4-triazol-1-yl)-4-cyclopropyl-butan-4-one of melting point 173° to 175° C. were obtained.

The following compounds of the formula $$R^1-CO-CH-\underset{\underset{N}{|}}{CH}-R^2 \quad (I)$$
(with triazole)

which are listed in Table 2 were obtained in a corresponding manner:

TABLE 2

| Compound No. | $R^1$ | $R^2$ | Melting point (°C.) |
|---|---|---|---|
| 4 | ⟨CH₃ cyclopropyl⟩ | —CCl₂CH₃ | 196–98 |
| 5 | ⟨CH₃ cyclopropyl⟩ | —CCl₂—C₂H₅ | 158–61 |
| 6 | ⟨CH₃ cyclopropyl⟩ | —CCl₂—i-C₃H₇ | 134–37 |

TABLE 2-continued

| Compound No. | $R^1$ | $R^2$ | Melting point (°C.) |
|---|---|---|---|
| 7 | ⟨CH₃ cyclopropyl⟩ | —CCl₂—CHCl—CH₃ | 178–79 |
| 8 | ⟨CH₃ cyclopropyl⟩ | —CCl₂—n-C₃H₇ | 161–62 |
| 9 | ⟨cyclopropyl⟩ | —CCl₂—CHCl—CH₃ | 56–62 |
| 10 | ⟨C₂H₅ cyclopropyl⟩ | —CCl₂—CH₂Cl | 194–196 |
| 11 | ⟨C₂H₅ cyclopropyl⟩ | —CCl₂—CH₂Cl | 185–187 |

The fungicidal and plant growth regulating activity of the compounds of this invention is illustrated by the following biotest examples.

In these examples, the compounds according to the present invention are each identified by the number (given in brackets) from the corresponding preparative example and Table 2.

The known comparison compounds are identified as follows:

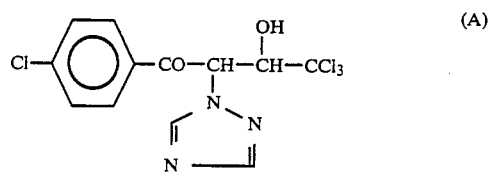
(A)

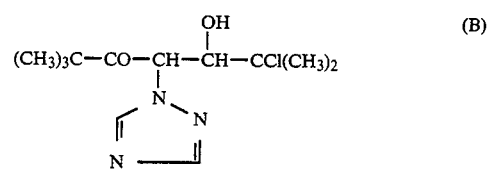
(B)

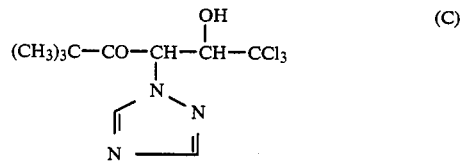
(C)

EXAMPLE A

Venturia test (apple)/protective

Solvent: 4.7 parts by weight of acetone

Emulsifier: 0.3 parts by weight of alkylaryl polyglycol ether

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous conidia suspension of the apple scab causative organism (Venturia inaequalis) and then remained in an incubation cabinet at 20° C. and 100% relative atmospheric humidity for 1 day.

The plants were then placed in a greenhouse at 20° C. and a relative atmospheric humidity of about 70%.

Evaluation was carried out 12 days after the inoculation.

In this test, a clearly superior activity compared with the prior art was shown, for example, by the compounds (1) and (2).

EXAMPLE B

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were dusted with conidia of the fungus Sphaerotheca fuliginea.

The plants were then placed in a greenhouse at 23° to 24° C. and at a relative atmospheric humidity of about 75%.

Evaluation was carried out 10 days after the inoculation.

In this test, a clearly superior activity compared with the prior art was shown, for example, by the compound (2).

EXAMPLE C

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (1), (2), (3) and (4).

EXAMPLE D

Erysiphe test (barley)/seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of Erysiphe graminis f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compound (2).

EXAMPLE E

Inhibition of growth of grass (Festuca pratensis)
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Grass (Festuca pratensis) was grown in a greenhouse up to a height in growth of 5 cm. In this stage, the plants were sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

In this test, the compound (3) showed a powerful inbibition of growth.

EXAMPLE F

Inhibition of growth of barley
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. In this stage, the plants were sprayed with the preparations of active compound until dripping wet. After 3 weeks, the additional growth was measured on all plants and the inhibition of growth in percent of the additional growth of the control plants was calculated. 100% inhibition of growth meant that growth had stopped and 0% denoted a growth corresponding to that of the control plants.

In this test, the compound (3) showed a powerful growth-inhibiting action.

EXAMPLE G

Influence on growth of sugar beet
Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, while positive values characterized a promotion of growth in comparison to the control plants.

In this test, the compound (3) showed a powerful growth-inhibiting action.

It will be appreciated that the instant specification and examples are set forth by way of illustration and not limitation, and that various modifications and changes may be made without departing from the spirit and scope of the present invention.

We claim:

1. A cycloalkyl(α-triazolyl-β-hydroxy)-ketone of the formula

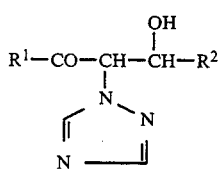

in which

R¹ is cyclopropyl or 1-methyl-cyclopropyl, and

R² is a trichloromethyl, dichlorofluoromethyl, trifluoromethyl, dichloromethyl, chloromethyl, 1,1,2-trichloroethyl, 1,1-dichloroethyl, 1,1-dibromoethyl, 1,1-dichloropropyl, 1,1-dichlorobutyl, 1,1,2-trichloropropyl, 2-chloro-prop-2-yl, 1,2,2-trichlorovinyl, 2,2-dichlorovinyl or 1,1-dichloro-2-methyl-propyl group, or an addition product thereof with a physiologically acceptable acid or a metal salt.

2. A compound according to claim 1, wherein such compound is 1,1,1-trichloro-2-hydroxy-3-(1,2,4-triazol-1-yl)-4-(1-methylcycloprop-1-yl)-butan-4-one of the formula

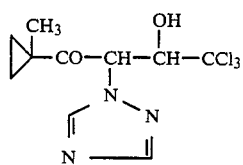

or an addition product thereof with a physiologically acceptable acid or a metal salt.

3. A compound according to claim 1, wherein such compound is 1,2,2-trichloro-3-hydroxy-4-(1,2,4-triazol-1-yl)-5-(1-methylcycloprop-1-yl)-pentan-5-one of the formula

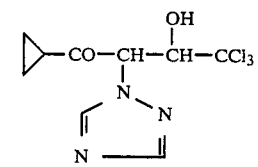

or an addition product thereof with a physiologically acceptable acid or a metal salt.

4. A compound according to claim 1, wherein such compound is 1,1,1-trichloro-2-hydroxy-3-(1,2,4-triazol-1-yl)-4-cyclopropyl-butan-4-one of the formula

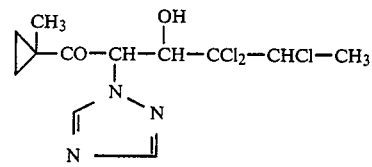

or an addition product thereof with a physiologically acceptable acid or a metal salt.

5. A compound according to claim 1, wherein such compound is 2,3,3-trichloro-4-hydroxy-5-(1,2,4-triazol-1-yl)-6-(1-methylcycloprop-1-yl)-hexan-6-one of the formula

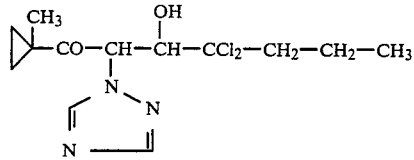

or an addition product thereof with a physiologically acceptable acid or a metal salt.

6. A compound according to claim 1, wherein such compound is 4,4-dichloro-5-hydroxy-6-(1,2,4-triazol-1-yl)-7-(1-methylcycloprop-1-yl)-heptan-7-one of the formula

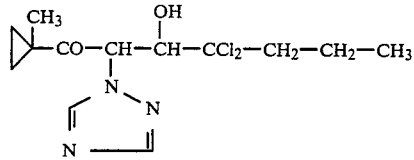

or an addition product thereof with a physiologically acceptable acid or a metal salt.

7. A fungicidal or plant-growth regulating composition, comprising a fungicidally or plant-growth regulating effective amount of a compound or addition product according to claim 1 in admixture with a diluent.

8. A method of combating fungi comprising applying to the fungi, or to a habitat thereof, a fungicidally effective amount of a compound or addition product according to claim 1.

9. A method of regulating the growth of plants comprising applying to the plants, or to a habitat thereof, a plant-growth regulating effective amount of a compound or addition product according to claim 1.

10. The method according to claim 8, wherein such compound is 1,1,1-trichloro-2-hydroxy-3-(1,2,4-triazol-1-yl)-4-(1-methylcycloprop-1-yl)-butan-4-one, 1,2,2-trichloro-3-hydroxy-4-(1,2,4-triazol-1-yl)-5-(1-methylcycloprop-1-yl)-pentan-5-one, 1,1,1-trichloro-2-hydroxy-3-(1,2,4-triazol-1-yl)-4-cyclopropyl-butan-4-one, 2,3,3-trichloro-4-hydroxy-5-(1,2,4-triazol-1-yl)-6-(1-methylcycloprop-1-yl)-hexan-6-one, or 4,4-dichloro-5-hydroxy-6-(1,2,4-triazol-1-yl)-7-(1-methylcycloprop-1-yl)-heptan-7-one.

11. A method of combating fungi comprising applying to the fungi, or to a habitat thereof, a fungicidally effective amount of a compound or addition product according to claim 2.

12. A method according to claim 9, wherein such compound is 1,1,1-trichloro-2-hydroxy-3-(1,2,4-triazol-1-yl)-4-(1-methylcycloprop-1-yl)-butan-4-one, 1,2,2-trichloro-3-hydroxy-4-(1,2,4-triazol-1-yl)-5-(1-methylcycloprop-1-yl)-pentan-5-one, 1,1,1-trichloro-2-hydroxy-3-(1,2,4-triazol-1-yl)-4-cyclopropyl-butan-4-one, 2,3,3-trichloro-4-hydroxy-5-(1,2,4-triazol-1-yl)-6-(1-methylcycloprop-1-yl)-hexan-6-one, or 4,4-dichloro-5-hydroxy-6-(1,2,4-triazol-1-yl)-7-(1-methylcycloprop-1-yl)-heptan-7-one.

* * * * *

UNITED STATES PATENT AND TRADEMARK OFFICE
CERTIFICATE OF CORRECTION

PATENT NO. : 4,530,715
DATED : July 23, 1985
INVENTOR(S) : Eckart Kranz, et al.

It is certified that error appears in the above-identified patent and that said Letters Patent is hereby corrected as shown below:

| | |
|---|---|
| Col. 6, line 51 | Delete "an" and substitute --and-- |
| Col. 12, line 26 | Insert -- - -- between "1" and "yl" |
| Col. 12, line 33 | Before structure insert -- a)-- |
| Col. 12, line 53 | Before structure insert -- b)-- |
| Col. 14, line 16 | Table 2, line 4 under "$R^2$" delete "$-CCl_2-CH_2Cl$" and substitute -- $-CCl_3$ -- |

Signed and Sealed this

Twenty-sixth Day of November 1985

[SEAL]

Attest:

Attesting Officer

DONALD J. QUIGG

Commissioner of Patents and Trademarks